US011925718B2

(12) United States Patent
Kleinmann

(10) Patent No.: US 11,925,718 B2
(45) Date of Patent: Mar. 12, 2024

(54) DECONTAMINATION ASSEMBLY

(71) Applicant: Metall + Plastic GmbH, Radolfzell (DE)

(72) Inventor: Stefan Kleinmann, Radolfzell (DE)

(73) Assignee: Metall + Plastic GmbH, Radolfzell (DE)

(*) Notice: Subject to any disclaimer, the term of this patent is extended or adjusted under 35 U.S.C. 154(b) by 47 days.

(21) Appl. No.: 16/091,649

(22) PCT Filed: Dec. 8, 2016

(86) PCT No.: PCT/EP2016/080337
§ 371 (c)(1),
(2) Date: Oct. 5, 2018

(87) PCT Pub. No.: WO2017/174169
PCT Pub. Date: Oct. 12, 2017

(65) Prior Publication Data
US 2019/0151488 A1 May 23, 2019

(30) Foreign Application Priority Data
Apr. 7, 2016 (DE) .................. 10 2016 106 407.6

(51) Int. Cl.
*A61L 2/20* (2006.01)
*A61L 2/22* (2006.01)
(Continued)

(52) U.S. Cl.
CPC ............. *A61L 2/208* (2013.01); *A61L 2/22* (2013.01); *A61L 2/26* (2013.01); *G21F 7/04* (2013.01);
(Continued)

(58) Field of Classification Search
CPC ... A61L 2/208; A61L 2/26; A61L 2/22; A61L 2202/12; A61L 2202/15; A61L 2202/21;
(Continued)

(56) References Cited

U.S. PATENT DOCUMENTS

| 6,010,400 A * | 1/2000 | Krainiak ............ A61L 2/24 454/187 |
| 2013/0004390 A1* | 1/2013 | Von Stenglin ........ A61L 2/20 423/210 |

FOREIGN PATENT DOCUMENTS

| CH | 705249 A1 | 1/2013 |
| EP | 2719962 A1 | 4/2014 |

(Continued)

OTHER PUBLICATIONS

Translation of Specification of Sigwarth (Year: 2013).*
International search report for patent application No. PCT/EP2016/080337 dated Mar. 5, 2017.

*Primary Examiner* — Sean E Conley
*Assistant Examiner* — Brendan A Hensel
(74) *Attorney, Agent, or Firm* — Bachman & LaPointe, P.C.

(57) ABSTRACT

A decontamination assembly (1) for pharmaceutical applications, comprising an isolator (2) having a manipulator chamber (3) and a plenum chamber (4) which is disposed above the manipulator chamber (3) and which can be supplied with an air flow (9) via at least one circulation fan (7) disposed in a circulating-air generation chamber, a membrane (5) for generating a laminar air flow (11) in the manipulator chamber (3) during a working operating state being disposed between the plenum chamber (4) and the manipulator chamber (3), the manipulator chamber (3) being connected to the circulating-air generation chamber (6) in an air-conducting manner via a return-air channel (12), further comprising ultrafine distributing means (19), for producing (Continued)

a decontaminant/air mixture based on a liquid decontaminant stock, a stock of $H_2O_2$, the ultrafine distributing means (19) being connected to the plenum chamber (4) via at least one plenum supply line (25) leading into the plenum chamber (4) so as to directly supply the plenum chamber (4) with the decontaminant/air mixture when in a decontamination operating state, wherein the ultrafine distributing means (19) are connected directly to the manipulator chamber (3) via at least one manipulator supply line (27) so as to directly supply the manipulator chamber (3) with the decontaminant/air mixture when in the decontamination operating state.

19 Claims, 2 Drawing Sheets

(51) Int. Cl.
*A61L 2/26* (2006.01)
*G21F 7/04* (2006.01)

(52) U.S. Cl.
CPC ........ *A61L 2202/11* (2013.01); *A61L 2202/12* (2013.01); *A61L 2202/122* (2013.01); *A61L 2202/15* (2013.01); *A61L 2202/21* (2013.01)

(58) Field of Classification Search
CPC ... A61L 2202/11; A61L 2202/122; G21F 7/04
See application file for complete search history.

(56) References Cited

FOREIGN PATENT DOCUMENTS

| | | |
|---|---|---|
| WO | 2011085735 A1 | 7/2011 |
| WO | 2013003967 A1 | 1/2013 |
| WO | 2014079779 A1 | 5/2014 |

\* cited by examiner

DECONTAMINATION ASSEMBLY

BACKGROUND OF THE INVENTION

The invention relates to a decontamination assembly as disclosed herein, in particular for pharmaceutical applications, comprising an isolator having a manipulator chamber (also referred to as a working chamber or space) and a plenum chamber (intermediate space) which is disposed above the manipulator chamber (along a vertical) and which can be supplied with an air flow via at least one circulation fan disposed in a circulating-air generation chamber, a membrane, in particular a mesh, for generating a laminar air flow in the manipulator chamber (from the air flow flowing into the plenum chamber) during a working operating state being disposed between the plenum chamber and the manipulator chamber, the manipulator chamber being connected to the circulating-air generation chamber in an air-conducting manner via a return-air channel which is preferably disposed between two transparent plates, further comprising ultrafine distributing means, in particular an evaporator or nebulizer, for producing a decontaminant/air mixture based on a liquid decontaminant stock, preferably a stock of $H_2O_2$, the ultrafine distributing means being connected to the plenum chamber via at least one plenum supply line leading into the plenum chamber so as to directly supply the plenum chamber with the decontaminant/air mixture when in a decontamination operating state.

Furthermore, the invention relates to a method according to the preamble of claim 14 for operating a decontamination assembly of this kind.

In WO 2011/085735 A1 and EP 2 719 962 A1, a decontamination assembly comprising an incubator and an $H_2O_2$ evaporator is described. The $H_2O_2$ evaporator (flash evaporator) is connected directly to a plenum chamber, which is referred to as an intermediate space in the cited document, via a plenum supply line, the plenum chamber being separated from a manipulator chamber located below via a membrane for generating a laminar air flow. In a decontamination phase, a decontaminant/air mixture is introduced into the plenum chamber via the plenum supply lines. At the same time, an exhaust air line from a circulating-air generation chamber located above the plenum chamber is open, allowing the decontaminant/air mixture to slowly travel into the manipulator chamber through the membrane and into the circulating-air generation chamber via lateral return air channels. The disadvantage of the known method is the relatively long decontamination time that is needed to ensure sufficiently long contact—in particular of the lower region of the manipulator chamber—with the decontaminant/air mixture.

From WO 2013/003967 A1 and from its priority application CH 705 249 A1, different embodiment variations of decontamination assemblies comprising an $H_2O_2$ nebulizer and an incubator are known. A described first option of placing the nebulizer is to dispose the nebulizer in the manipulator chamber (referred to as a working chamber). Alternatively, the nebulizer can be disposed outside of and adjacent to the working chamber and to introduce the decontaminant/air mixture directly into the working chamber. Another described alternative intends for the nebulizer to be disposed directly within the circulating-air generation chamber. The circulation fan is operated to distribute the decontaminant/air mixture.

From U.S. Pat. No. 6,010,400 A, it is known for air to be transported through an evaporator during circulating-air operation, i.e. for the evaporator to not be supplied with sterile air externally, the resulting decontamination/air mixture being introduced directly into a manipulator chamber, bypassing a catalyst-impregnated high-performance filter for suspended particles in an area above the manipulator chamber.

In the known decontamination assembly, the circulation fan is not located in a circulating-air generation chamber in an area above the manipulator chamber, but is disposed on the side in a pipeline system.

SUMMARY OF THE INVENTION

Based on the aforementioned state of the art, the object of the invention is to provide a decontamination assembly which has a plenum chamber disposed above a manipulator chamber and separated from the manipulator chamber by a membrane for generating a laminar flow in the manipulator chamber (working chamber) and in which the decontamination time, i.e. the time of subjection to a decontaminant/air mixture, is reduced.

Furthermore, the object is to provide a method for operating a decontamination assembly of this kind, the method to be characterized by a shortened decontamination operating state.

With regard to the decontamination assembly, said object is attained by the features disclosed herein, i.e. by a generic decontamination assembly having the ultrafine distributing means connected directly to the manipulator chamber via at least one manipulator supply line so as to directly supply the manipulator chamber with the decontaminant/air mixture when in the decontamination operating state.

With regard to the method, said object is attained by the features as disclosed herein, i.e. by additionally supplying the manipulator chamber directly with the decontaminant/air mixture, specifically via at least one manipulator supply line which leads directly into the manipulator chamber and which connects the ultrafine distributing means directly to the manipulator chamber, in a generic method in which the plenum chamber is subjected directly to the decontaminant/air mixture.

Advantageous embodiments are indicated in the dependent claims. Any and all combinations of at least two of the features disclosed in the description, the claims, and/or the figures fall within the scope of the invention. To avoid redundancies, features disclosed in accordance with the device shall also be considered disclosed and claimable in accordance with the method. Likewise, features disclosed in accordance with the method shall also be considered disclosed and claimable in accordance with the device.

The invention is based on the idea of connecting the ultrafine distributing means both to the plenum chamber via a plenum supply line (direct line) which leads directly into the plenum chamber above the membrane and has an outlet there, and directly to the manipulator chamber via at least one manipulator supply line (direct line). The plenum supply line leads directly into the plenum chamber, i.e. preferably not into any (other) feed or discharge line to or from the plenum chamber. Analogously, the manipulator supply line leads directly into the manipulator chamber, i.e. not into a feed or discharge line to or from the manipulator chamber (working chamber). Of course, additional feed or discharge lines of this kind can be provided if required. The core idea of the invention, however, is for the ultrafine distributing means to be connected directly and immediately to both the plenum chamber and the manipulator chamber so that, preferably simultaneously, both the plenum chamber and the manipulator chamber can be supplied with and are subjected to a decontaminant/air mixture from the ultrafine distributing means.

Consequently, the core idea of the invention is for the decontaminant/air mixture to be injected into not only a single functional chamber of the incubator (isolator) of the decontamination assembly and to then be distributed into the other chambers from said chamber, but to be injected directly into the two chambers separated by the laminarization membrane, namely the plenum chamber, which is preferably located below the circulation fan, and the manipulator chamber, which is located below the plenum chamber along the vertical, so as to achieve quicker distribution of the decontaminant/air mixture and thus significantly shorten the decontamination phase.

The substantial advantage of the decontamination assembly according to the invention and of the operating method according to the invention for an assembly of this kind is that owing to the direct connection of both the plenum chamber and the manipulator chamber to the ultrafine distributing means, quick contacting of all relevant areas with the decontaminant/air mixture can be achieved without having to switch the circulation fan on to do so. Hence, the latter is preferably switched off during the decontamination phase (time from the start of the introduction of the decontaminant/air mixture to the start of the purging phase)—at least during the major part or period of the decontamination phase—and distribution of the decontaminant/air mixture in the isolator (=incubator) is achieved simply by introducing the decontaminant/air mixture both in the plenum chamber and in the manipulator chamber with the aid of external carrier air and by opening an exhaust air channel from the isolator, via which the carrier air volume supplied via the ultrafine distributing means can be discharged from the isolator to the outside either immediately or via a catalytic convertor for degrading decontaminant. This embodiment allows for a preferred design or enhancement of the decontamination assembly, which will be explained later and in which at least one catalytic converter for degrading decontaminant during circulating-air operation in a purging phase following the decontamination phase or the decontamination operating state can be assigned to the at least one circulation fan. This is advantageous because operating the circulation fan of such an assembly to distribute the decontaminant/air mixture during the decontamination phase without a bypass being provided would lead to undesired premature degradation of the decontaminants during the decontamination phase.

Another advantage of non-operation of the circulation fan during at least the major part of the decontamination phase is that a high-performance filter for suspended particles, which preferably separates the circulation fan from the plenum chamber, comes into contact with the decontaminant/air mixture substantially from below only, i.e. at the surface of contact with the plenum chamber, during the decontamination phase and is not flushed with the decontaminant/air mixture; this is advantageous because flushing of this kind would disadvantageously necessitate longer purging because the high-performance filter for suspended particles would absorb decontaminant, which would then continue to evaporate from the high-performance filter for suspended particles, which is in particular a HEPA or ULPA filter, for some time.

The inventor has found that when $H_2O_2$ vapor outlets were disposed above the membrane as per the prior art, the membrane in the plenum chamber caused still turbulent flows to become laminarized (which is the task of the membrane in production operation, after all), which resulted in long distributing times in the manipulator chamber. By discharging $H_2O_2$ both in the plenum chamber and in the manipulator chamber as per the invention, turbulent flow conditions can be established in both chambers, in particular by discharging $H_2O_2$ at multiple different locations distributed across each chamber, to which end it is preferred for high exit velocities of pressurized air (carrier air) containing $H_2O_2$ to be realized in the plenum chamber and in the manipulator chamber, as will be explained later. Direct establishment of turbulent flow conditions by the exiting pressurized fluid containing $H_2O_2$ additionally renders the use of what is known as turbulators in the form of small (turbulence) fans disposed directly in the manipulator chamber unnecessary, which, in turn, means that particle introduction by rotating mechanical components can be avoided.

Comparative tests performed by the applicant have shown that using the device according to the invention and the method according to the invention, the cycle time can be reduced by more than 50% and the amount of hydrogen peroxide consumed in order to achieve the same concentration of hydrogen peroxide can also be reduced by more than 50%, specifically by 43% as measured in comparative tests.

In conclusion, the present invention is the first one to take the approach of directly supplying both the plenum chamber and the manipulator chamber with the decontaminant/air mixture, in particular an $H_2O_2$/air mixture, via at least one direct line or supply line each, the respective supply line leading directly into the corresponding chamber, i.e. the plenum chamber or the manipulator chamber, preferably via a nozzle, which will be explained later.

It should be noted at this point that even a combination of above-cited documents WO 2011/085735 A1 and WO 2013/003967 A1 would not have given the person skilled in the art any cause to connect the ultrafine distributing means to both the plenum chamber and the manipulator chamber. For instance, the document cited first deals exclusively with the introduction of hydrogen peroxide into the plenum chamber, which appeared perfectly sufficient at the time because the $H_2O_2$ vapor spread into the manipulator chamber from the top to the bottom through the membrane. WO 2013/003967 A1, on the other hand, does not use a decentral $H_2O_2$ evaporator, but a nebulizer, through whose use hydrogen peroxide does not transition to the gas phase, but merely becomes dispersed into ultrafine droplets. Nebulizers of this kind are not combined with evaporators in the same installation—they represent different ultrafine distribution concepts. According to the teaching of cited document WO 2013/003967 A1 (cf. feature d)) of claim 1, the nebulizer as a whole is installed on or in the so-called containment as an integral part of the known decontamination device, different installation sites such as alternatively in the plenum chamber or in the manipulator chamber being described. Because of the fact alone that the nebulizer unit is described as an inseparable unit which produces the $H_2O_2$ fog at only a single location in each case, the person skilled in the art had no cause to envisage a separation or distribution between two different chambers. The person skilled in the art has even less cause to assign outlets or outflow openings, in particular nozzles, to the ultrafine distributing means at multiple different locations within the manipulator chamber in order to assign a discharge of $H_2O_2$ immediately at or in the vicinity of critical areas, as is intended by embodiments of the invention and will be described in the following.

As mentioned, the manipulator chamber is a working chamber in which the actual application, preferably a pharmaceutical application, takes place. Preferably, a pharmaceutical production installation for at least partial production of a drug or medical agent and/or for metering and/or portioning of a drug or medical agent and/or for packaging a drug or medical agent is located in the manipulator chamber.

The plenum chamber located above the manipulator chamber along a vertical substantially serves to distribute air of an air flow supplied via at least one circulation fan disposed in a circulating-air generation chamber preferably disposed above the plenum chamber along the vertical. The air flow will flow from the plenum chamber into the manipulator chamber via the membrane, the membrane generating a preferably vertical laminar air flow, said air flow further preferably having an air velocity of 0.45 m/s. In the manipulator chamber, the laminar air flow will flow from the top to the bottom and into a lower area laterally toward at least one return-air channel which is preferably disposed between two preferably vertical transparent plates, allowing the operator to see into the interior of the manipulator chamber from the outside through the return-air channel. Preferably, but not necessarily, at least one port preferably penetrating the plates delimiting the return-air channel is assigned to the manipulator chamber, a glove by means of which the operator can manually reach into the manipulator or working chamber from the outside being disposed at the port. The return-air channel, in turn, preferably leads into the circulating-air generation chamber, which is preferably disposed above the plenum chamber along the vertical and in which the at least one circulation fan is located, to which a catalytic converter for degrading decontaminant during a purging phase after the decontamination operating state is preferably, but not necessarily, assigned. Preferably, the circulating-air generation chamber is, in turn, separated from the plenum chamber by at least one high-performance filter for suspended particles. The isolator additionally comprises at least one exhaust air line, which preferably branches off from the circulating-air generation chamber, the exhaust air line, as mentioned, being preferably open during the decontamination phase at least while the decontaminant/air mixture is being supplied so as to be able to discharge the supplied carrier volume. Furthermore, the isolator preferably comprises at least one supply air line via which sterile conditioned fresh air, in particular temperature-controlled and/or dried sterile fresh air, can be supplied.

It has proven particularly advantageous if multiple supply lines which lead into the plenum chamber at different locations and via which the plenum chamber can be and is supplied with the decontaminant/air mixture are provided. Preferably, the outlets of the supply lines are distributed evenly across the surface of the membrane so as to allow proper distribution. In principle, it is possible to route all supply lines directly, i.e. as far as to the ultrafine distributing means; however, an embodiment variation in which the plenum supply lines branch off from a distributing section of a main line which, in turn, leads directly to the ultrafine distributing means is preferred. Additionally or alternatively, it is preferred if not only a single one, but multiple manipulator supply lines lead into the manipulator chamber in order to achieve ideal distribution of the decontaminant/air mixture here, too. In this context, too, is also conceivable for all manipulator supply lines to be routed directly up to the ultrafine distributing means, it being preferred if the manipulator supply lines branch off from a main line or a supply line section that is connected directly to the ultrafine distributing means. Regarding the disposition of the at least one manipulator supply line, preferably of the multiple manipulator supply lines, it has proven advantageous if they are disposed in the area of the lateral incubator (isolator) or manipulator chamber walls extending in the vertical direction and inject the decontaminant/air mixture into the interior of the manipulator chamber from the side. Preferably, no working or functional unit is disposed below the outlets of the manipulator supply line, particle contamination thus being securely avoided.

A configuration of the decontamination assembly in which the plenum chamber and the manipulator chamber can be and are simultaneously supplied with the decontaminant/air mixture directly via the at least one plenum supply line and the at least one manipulator supply line during at least part of the decontamination phase is particularly preferred. Additionally or alternatively, if the decontamination assembly is configured accordingly, it is possible for the plenum chamber and the manipulator chamber to be supplied with the decontaminant/air mixture in a cycled or alternating manner during part of the decontamination phase.

During the working operating state, which follows a purging operating state and during which preferably pharmaceutical functional or working units are operated in the manipulator chamber, the plenum chamber is pressurized compared to the manipulator chamber or, in other words, pressure occurs in the plenum chamber because the membrane for laminarizing the air flow causes flow resistance. In order to prevent air from flowing backward out of the plenum chamber via the plenum supply line and the manipulator-chamber supply line into the manipulator chamber because of said pressure and thereby disturbing the preferably vertical laminar air flow through the membrane, an embodiment of the invention intends for such a disturbing air flow to be prevented. In the preferred case in which the plenum supply line and the manipulator supply line are supplied by a shared supply line section or, in other words, the plenum supply line and the manipulator supply line have a shared line section, the disturbing air flow can be prevented by valve means which are configured and disposed accordingly and which can be actuated and controlled by control means and/or manually in such a manner that they interrupt the connection between the plenum supply line and the manipulator supply line during the working operating state, the connection preferably being open at least temporarily during the decontamination phase in order to ensure that the plenum chamber and the manipulator chamber are simultaneously supplied with the decontaminant/air mixture. Alternatively, it is possible for separate evaporators or nebulizers to be provided for the manipulator for supplying the manipulator supply line and the plenum supply line, i.e. for a direct air-conducting connection between the plenum supply line and the manipulator supply line to be omitted.

In particular in order to prevent the aforementioned disturbing air flow and/or to allow cycled operation or a cycled or alternating supply of the plenum chamber and of the manipulator chamber with the decontaminant/air mixture and/or to vary the volumetric flow rate of the decontaminant/air volumetric flow flowing through the at least one plenum-chamber supply line and of the decontaminant/air volumetric flow flowing through the at least one manipulator supply line. In an embodiment of the invention, during the decontamination phase, in particular, a plenum valve is assigned to the at least one plenum supply line, preferably upstream of the split into multiple supply lines, in particular in a distributor area, and/or a manipulator valve is assigned to the at least one manipulator supply line, preferably in an area upstream of the split into multiple manipulator supply lines. The plenum valve and/or the manipulator valve can be actuated via a controlling unit and/or manually according to the at least one objective mentioned above.

As mentioned, it is particularly preferred if the circulating-air generation chamber is separated from the plenum chamber by at least one high-performance filter for suspended particles via which the at least one circulation fan supplies the plenum chamber with the air flow. In the preferred case, in which the circulation fan is switched off for the major part of the decontamination phase (decontamination operating state), heavy "loading" or burdening of the high-performance filter for suspended particles with decontaminants is prevented. This is advantageous because sufficient sterility of the decontamination assembly can generally be achieved if only the contact side of the high-performance filter for suspended particles, i.e. the underside facing the plenum chamber, is decontaminated.

It is particularly advantageous if at least one catalytic converter for degrading decontaminant during circulating-air operation in a purging phase following the decontamination phase is assigned to the circulation fan controllable via controlling means. In the preferred case, in which the catalytic converter is stationary relative to the circulation fan without a bypass option being provided, the circulation fan preferably remains switched off at least during the major part of the decontamination phase in order to prevent degradation of decontaminant in the catalytic converter during the decontamination phase. Operation of the circulation fan during the decontamination phase, in particular during the major part of the decontamination phase, for further optimization of the distribution of the decontaminant/air mixture in the entire catalytic converter is possible and intended according to an embodiment of the invention if a bypass preventing passage through the catalytic converter while the circulation fan is being operated in the decontamination phase can be established between the catalytic converter and the circulation fan, preferably by actively shifting the catalytic converter or of the air-conducting means assigned thereto. Said bypass is preferably closed during the purging phase for degradation of the decontaminant.

As indicated in the beginning, the at least one plenum supply line and/or the at least one manipulator supply line leads into the plenum chamber and into the manipulator chamber, respectively, via at least one (exit) nozzle, the respective nozzle having multiple exit openings, which point in different directions. An embodiment is particularly preferred in which multiple plenum supply lines each lead into the plenum chamber via at least one (exit) nozzle and/or multiple manipulator supply lines each lead into the manipulator chamber via at least one (exit) nozzle, meaning that multiple (exit) nozzles are provided in the plenum chamber and/or in the manipulator chamber. Particularly good experiences were made with a nozzle design variation that has a cone section, in particular at the end, and a cylinder section adjacent thereto, in particular a rearward cylinder section, exit openings being provided both in the cone section and in the cylinder section.

With regard to the disposition of the outlets, in particular exit nozzles for carrier air (pressurized air) containing $H_2O_2$, it has proven advantageous with respect to the manipulator chamber to dispose such outlets, in particular nozzles, in the area of manipulator chamber corners, a manipulator corner referring to inner corners between two outer walls delimiting the manipulator chamber and preferably disposed at an angle of 90°. Preferably, one nozzle in particular is disposed in one corner in such a manner that the outlet or nozzle points from the corner in the direction of the interior of the manipulator chamber, in particular in the direction of a center of the manipulator chamber. It is particularly preferred if the outlet or nozzle is disposed at the same angle, in particular 45°, to both of the manipulator chamber walls forming the corner. With regard to the disposition of the outlets, in particular nozzles, with respect to the vertical direction, it has proven advantageous if the outlets, in particular nozzles, are disposed above half of the height, in particular above ⅔ of the height of the manipulator chamber as measured from a manipulator chamber bottom up to the membrane delimiting the manipulator chamber from the plenum chamber. In a particularly preferred manner, the outlets or nozzles are disposed in such a manner with respect to manipulator chamber fixtures, such as handling apparatus for handling pharmaceuticals, that the nozzles are located on a height level above the fixtures, but not immediately above a product path, but instead offset to the side relative thereto.

It has proven particularly advantageous if 0.5 to 2.0 nozzles, in particular 0.7 to 1.6 nozzles per square meter of the inner manipulator-chamber base area (ground area) and/or between 0.5 and 2.5, in particular between 0.8 and 1.5 nozzles per square meter of the inner manipulator-chamber base area (ground area) of the manipulator chamber are disposed within the plenum chamber.

It has proven particularly advantageous if at least one of the aforementioned exit nozzles, preferably several of the aforementioned exit nozzles, more preferably all of the aforementioned exit nozzles are pressurized in such a manner that the fluid supplied to them via a plenum supply line or a manipulator supply line is pressurized, in particular by use of sterile pressurized air as carrier air for $H_2O_2$ vapor or $H_2O_2$ fog, so that turbulent flow conditions which ensure ideal distribution of the hydrogen peroxide vapor or fog in the plenum and manipulator chambers exist at at least one exit opening, preferably at several exit openings, of the at least one nozzle. It is particularly preferred if the exit velocity of the pressurized air containing $H_2O_2$ at the at least one exit nozzle, in particular at an exit opening of the nozzle in the plenum chamber, preferably at each of the multiple exit nozzles in the plenum chamber, is between 5.0 m/s and 80 m/s, particularly preferably between 8.0 m/s and 50 m/s, and/or the exit velocity of the pressurized air containing $H_2O_2$ at the at least one exit nozzle in the manipulator chamber, preferably at multiple exit nozzles in the manipulator chamber, is between 8.0 m/s and 100 m/s, particularly preferably between 12.0 m/s and 80 m/s.

As indicated before, an embodiment variation in which the ultrafine distributing means are connected to a carrier air line via which the ultrafine distributing means are supplied with carrier air (pressurized air) from outside of the working chamber is preferred. Preferably, this carrier-air volumetric flow is greater than 40 m³/h, particularly preferably greater than 70 m³/h, even more preferably between 75 m³/h and 120 m³/h, and, mixed with contaminant vapor or fog, is distributed to the plenum chamber and to the manipulator chamber via the at least one plenum supply line and the at least one manipulator supply line.

BRIEF DESCRIPTION OF THE DRAWINGS

Other advantages, features and details of the invention are apparent from the following description of a preferred embodiment and from the drawing.

FIG. 1: shows a decontamination assembly configured according to the concept of the invention and, on the left, an enlarged illustration of a preferred exit nozzle for a decontaminant/air mixture and, on the right, a distributing section or manifold for distributing the decontaminant/air volumetric flow to multiple manipulator supply lines.

DETAILED DESCRIPTION

Figure 1:
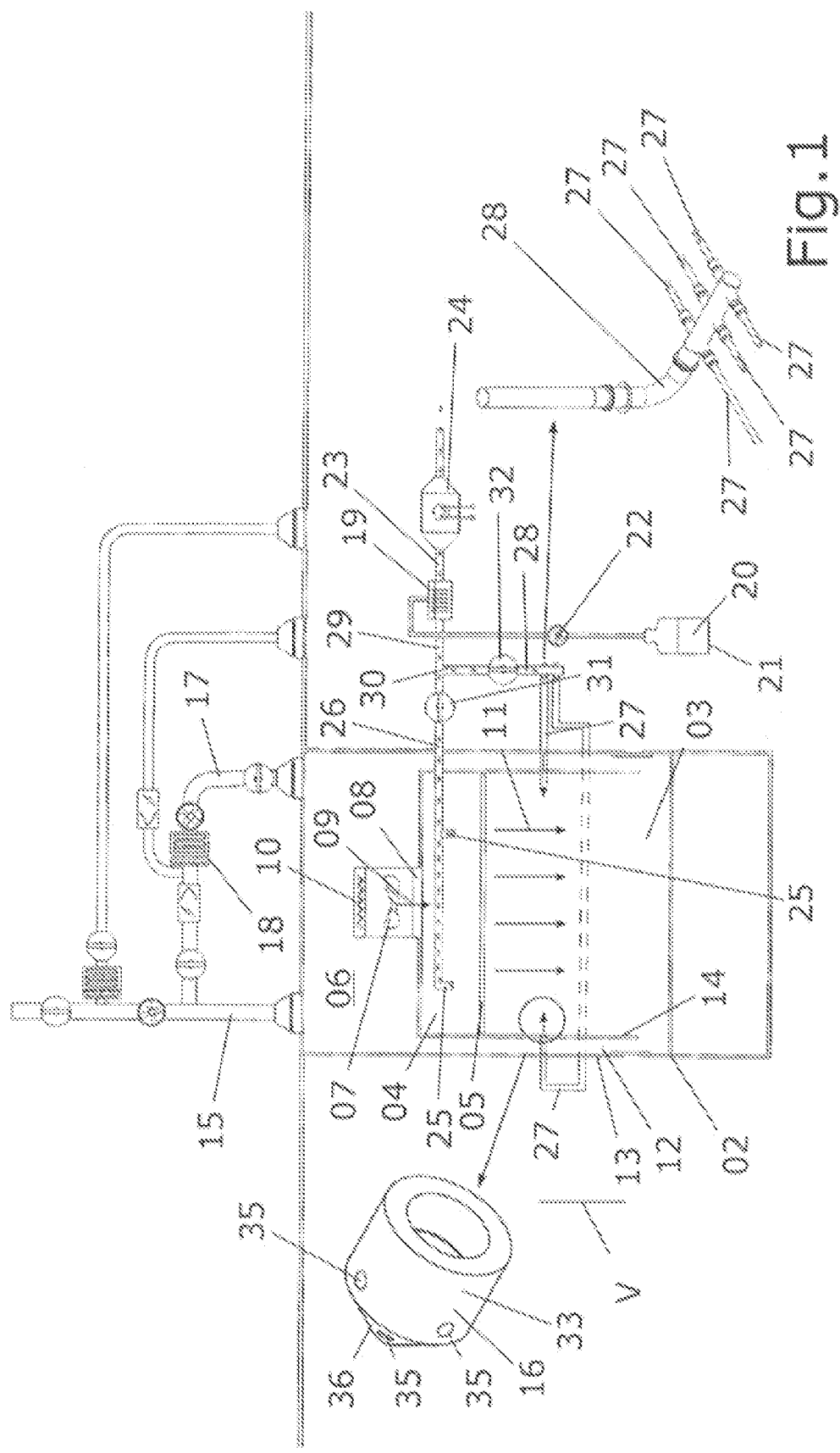

FIG. 1 shows a decontamination assembly 1 configured according to the concept of the invention. It comprises an isolator 2 for pharmaceutical applications which has a manipulator chamber 3 (working chamber) in which pharmaceutical working and/or functional units (not shown) for producing, metering and/or packaging a pharmaceutical agent are located.

Along a vertical V, a so-called plenum chamber 4 (air distribution chamber) which is separated from the manipulator chamber 3 by a horizontally extending membrane 5 is located above the manipulator chamber 3. Again along the vertical, a circulating-air generation chamber 6 having a circulation fan 7 for generating a circulating-air volumetric flow is located above the plenum chamber 4. The circulating-air generation chamber 6 is separated from the plenum chamber 4 by a high-performance filter 8 for suspended particles via which the plenum chamber 4 can be supplied with an air flow 9 from the circulation fan 7. A catalytic converter 10, such as a MnO2-based catalytic converter 10 for degrading decontaminant—$H_2O_2$ in this case—during a purging phase, is located upstream of the circulation fan 7 by way of example (additionally or alternatively downstream of the circulation fan 7).

As mentioned, the air flow supplied to the plenum chamber 4 flows via the membrane 5 into the circulating-air generation chamber 6, whereby a laminar air flow 11 flowing from the top to the bottom in the vertical direction and having an air flow velocity of 0.45 m/s is generated in the working chamber or manipulator chamber 3. As mentioned, the laminar air flow 11 flows from the top to the bottom and then, in a lower area, outward or laterally toward at least one inlet of at least one return-air channel 12 which, in the embodiment shown, is formed between two transparent plates 13, 14 via which an operator can see into the manipulator chamber 3 from the outside. Preferably, said plates 13, 14 are penetrated by a glove port (not shown for the sake of clarity) for manually reaching into the manipulator chamber 3, which is not mandatory, however. The at least one return-air channel 12 leads upward along the vertical V into the circulating-air generation chamber 6, from which air for generating the air flow 9 and, subsequently, the laminar air flow 11 will be aspirated by the circulation fan 7 during its operation.

An exhaust air line 15 which is open during at least part of a decontamination phase in order to discharge a carrier-air volumetric flow in the direction of the surroundings branches off from the circulating-air generation chamber 6. Furthermore, a fresh air line 17 for supplying sterile conditioned air whose temperature and moisture content is adjusted to the desired values by corresponding conditioning means 18 leads into the circulating-air generation chamber 6.

To decontaminate the isolator 2 during a decontamination operating state, the decontamination assembly comprises ultrafine distributing means 19, here in the form of a single flash evaporator, for example, for evaporating decontaminant 20—here $H_2O_2$—from a stock 21. The decontaminant 20 is supplied to the evaporator 19 by means of a pump 22 and evaporated there, the decontaminant vapor being swept along by carrier air supplied via an external carrier air line 23. The carrier air is supplied externally and is sterilized, in particular by provision of at least one corresponding high-performance filter for suspended particles, before it enters the isolator 2. The carrier air is preferably temperature-controlled, in particular to a temperature of 45° C., and dried. To this end, a corresponding conditioner 24 is integrated in the carrier air line 23.

In the specific embodiment example, the ultrafine distributing means 19 are located outside of the functional chambers of the isolator 2, which is preferred; alternatively, they can be disposed in such a functional chamber.

Multiple plenum supply lines 25 which lead directly into the plenum chamber 4 are connected to the ultrafine distributing means 19 in a gas-conducting manner, allowing the decontaminant/air mixture to be injected directly into the plenum chamber 4 in an area above the membrane 5. The plenum supply lines 25 branch off from a plenum supply distributing line 26. Preferably, nozzles are located at the ends of the plenum supply lines 25.

Furthermore, multiple manipulator supply lines 27 which lead directly into the manipulator chamber 3 at the side, i.e. in the area of the inner walls of the manipulator chamber, are connected in a gas-conducting manner to the ultrafine distributing means 19—here the single and shared flash evaporator by way of example—allowing the decontaminant/air mixture to be discharged directly into the manipulator chamber 3 as well. The manipulator supply lines 27 branch off from a manipulator supply distributing line 28 (manifold). The manipulator supply distributing line 28 and the plenum supply distributing line 26 are supplied by a shared supply line 29, which thus forms part of both the plenum supply lines 25 and the manipulator supply lines 27. The supply line 29, which is connected directly to the ultrafine distributing means 19, splits into the plenum supply lines 25 and the manipulator supply lines 27 or into a main plenum supply line (plenum supply distributing line) and a main manipulator line (manipulator supply distributing line) at a junction 30. Valve means are provided in both main distributing lines. Specifically, a plenum valve 31 is assigned to the plenum supply lines 25 and a manipulator valve 32 is assigned to the manipulator supply lines 27. In principle, one of the two valves 31, 32 is sufficient to prevent a disturbing air flow from the plenum chamber 4 via the plenum supply lines 25 and the manipulator supply lines 28 into the manipulator chamber 3. Such a solution can be realized as well. The shown variation with two valves is preferred, however. By providing the valves, at least one of which is preferably configured as a proportional valve, the plenum chamber 4 and the manipulator chamber 3 can be supplied with the decontaminant/air mixture in a cycled manner, i.e. repeatedly one after the other in an alternating manner. Additionally or alternatively, it is possible for the volumetric flow rate of the volumetric flows flowing via the plenum supply lines 25 and the manipulator supply lines 28 to be varied, changing of the volumetric flow rate during the decontamination phase being particularly preferred.

Instead of the shown embodiment variation, it is conceivable that the manipulator supply lines 28 and the plenum supply lines 25 are supplied with a decontaminant/air mixture via separate evaporators or nebulizers. The variation with a shared evaporator or nebulizer is preferred, in which case at least one valve for suppressing the mentioned disturbing air flow is preferably provided.

On the left in the drawing plane according to FIG. 1, a preferred embodiment of the end-side nozzle 33 is shown; a decontaminant/air mixture flows in from the left to the right in the drawing plane, i.e. into the shown entry opening 34 and then via various exit openings 35 into the respective chamber, exit openings 35 which point in different directions being provided at both a front cone section 36 and a cylinder section 16 located behind it. Nozzles 33, preferably as shown, can be provided at the ends of both the manipulator supply lines 27 and the plenum supply lines 25.

On the right in the drawing plane, an embodiment variation of the manipulator supply distributing line 28 from the end of which various manipulator supply lines 27 branch off, which then end directly in the manipulator chamber 3, is shown enlarged.

During a decontamination phase, the exhaust air line 15 is open and carrier air flows via the carrier line 23 to the ultrafine distributing means 19, where it is charged with decontaminant in the form of vapor or fog, the resulting decontaminant/air mixture flowing directly into both the plenum chamber 4 and the manipulator chamber 3. The open exhaust air line 15 causes convection, and the mixture disperses in the plenum chamber 4, in the working chamber, in the return-air channels 12 and in the circulating-air generation chamber 6. The circulation fan 7 is switched off during the major part of said decontamination phase so as to prevent degradation of decontaminant in the catalytic converter 10. While the circulation fan 7 could be operated in an embodiment variation without the catalytic converter 10 disposed as shown, this is preferably prevented in order to, among other things, avoid excessive charging of the high-performance filter 8 for suspended particles. After the decontamination phase, which will entail exposure time in addition to the phase of supplying the decontaminant/air mixture, the circulation fan 7 is operated in the circulating-air mode to purge the isolator 2. If required, conditioned fresh air can be simultaneously supplied via the supply line 17 and exhaust air can then be discharged accordingly via the exhaust air line 15. The purging phase is followed by a working phase, in which the working and/or functional units (not shown) in the manipulator chamber 3 are operated. During said operation, the circulation fan 7 is operated and, as explained, generates the laminar air flow in the vertical direction. Disturbing air flows via the manipulator supply lines 27 are prevented by corresponding valve means.

The applicant carried out various tests to prove the surprisingly great advantages of the device according to the invention and of the method according to the invention in terms of reducing the (decontamination) cycle time and $H_2O_2$ consumption.

To this end, the applicant used a decontamination assembly as shown in FIG. 1, in which the supply of decontaminant directly into the manipulator chamber 3 was interrupted or blocked and decontaminant vapor was led into the plenum chamber 4 only (as per the state of the art) so as to simulate a decontamination assembly according to the state of the art. To determine the results of a method according to the invention, $H_2O_2$ vapor was discharged simultaneously into the manipulator chamber 3 and into the plenum chamber 4. The applicant found that in a mode of operation according to the invention, in which hydrogen peroxide vapor was introduced into both the plenum chamber and the manipulator chamber, hydrogen peroxide consumption could be reduced from 773 g to 473 g, i.e. by 43%, as compared to the variation according to the state of the art. Additionally, as can be seen from FIG. 2, which is to be explained below, the $H_2O_2$ injection phase C could be reduced from 57 min to 33 min, i.e. by 42%. Moreover, the purging time, i.e. the ventilation time, could be significantly shortened, which is apparent from a comparison of the dashed line with the dropping solid line. The applicant explains the latter effect by the reduced absolute amount of $H_2O_2$ needed.

Figure 2:
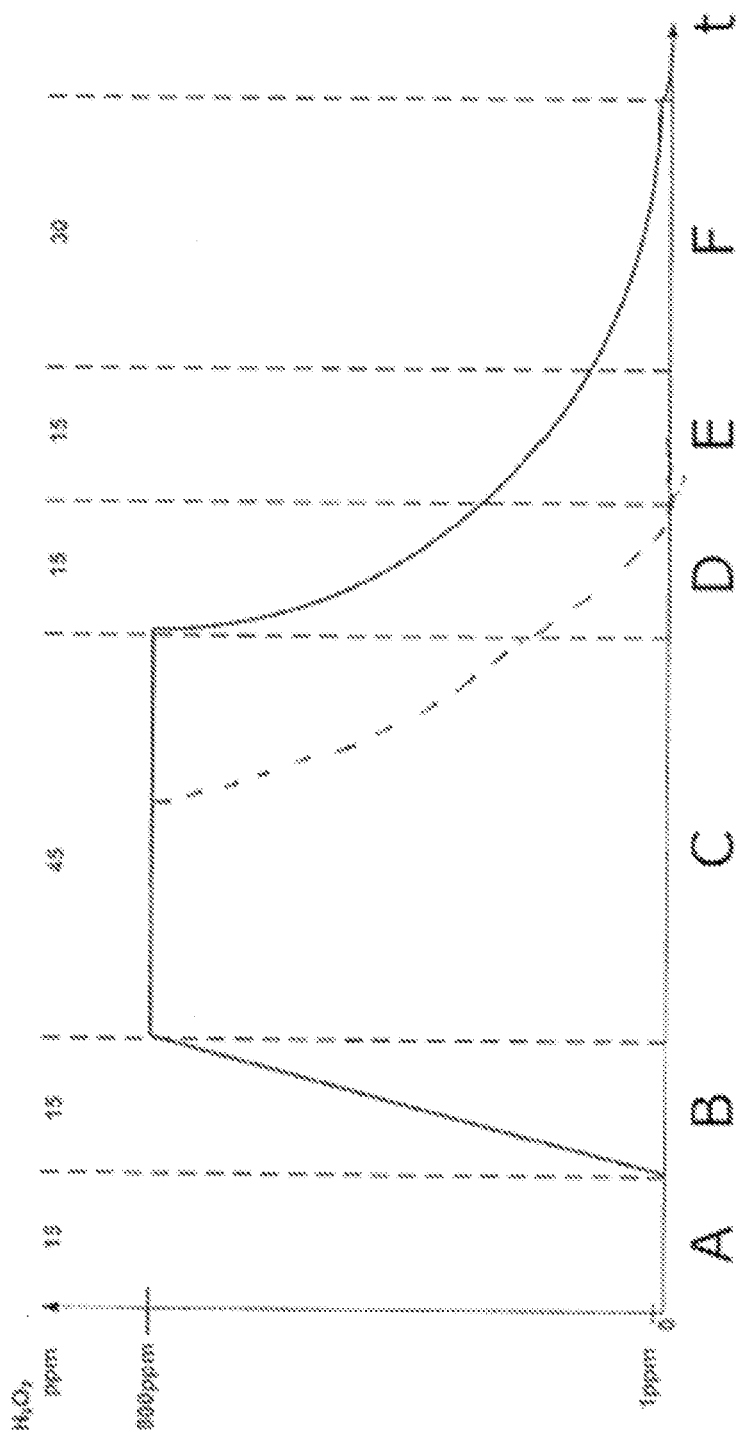
FIG. 2: is a diagram showing the hydrogen peroxide concentration during a decontamination cycle, specifically as compared between a known decontamination method and a decontamination method (dashed line) implemented according to the concept of the invention.

In the aforementioned diagram in FIG. 2, the $H_2O_2$ concentration in the manipulator chamber is indicated in ppm on the Y-axis, which is plotted over time (t) (X-axis). The time axis is divided into multiple functional times or sections. Phase A is a preconditioning phase, in which the interior volume of the isolator is pre-purged with conditioned, i.e. temperature-controlled and dehumidified, air. This is followed by a conditioning phase B of 15 min, in which the hydrogen peroxide concentration was increased to the desired concentration of 800 ppm. This is followed by the decontamination phase C, which, in the method according to the invention, lasts only until the beginning of the dashed line and is significantly shortened as compared to the method according to the state of the art (solid line). The phases D, E, and F are purging phases in the state of the art; in a method according to the invention, they begin at an earlier time and are not represented on the X-axis for the method according to the invention (dashed line) for reasons of clarity. In principle, these phases shift to the left as compared to the method according to the state of the art.

The aforementioned advantages are essentially traced back to the gas distribution improved according to the invention and to the preferred realization of turbulent flow conditions both in the plenum chamber and in the manipulator chamber.

To support the aforementioned test results, the applicant also compared the decimal reduction time (D-value) at different locations within the manipulator chamber between the configuration according to the state of art and the configuration according to the invention. The decimal reduction time (D-value) is the time in which $9/10$ of the population of a biological indicator dies off (of course the same bioindicator was used in the same locations in the comparative tests). None of the other parameters, such as temperature etc., were changed. The results confirm the advantageousness of a device according to the invention (decontamination assembly) and of a method according to the invention over the configuration according to the state of the art. Two test results are to be noted by way of example only. The D-value was examined with respect to two different critical bioindicator locations. In the configuration according to the invention, the D-value could be reduced from 5.2 min and 5.7 min, respectively, in the case of the variation according to the state of the art to less than 2 min each in the variation according to the invention.

REFERENCE SIGNS 1 decontamination assembly
2 isolator
3 manipulator chamber
4 plenum chamber
5 membrane
6 circulating-air generation chamber
7 circulation fan
8 high-performance filter for suspended particles
9 air flow
10 catalytic converter
11 laminar air flow
12 return-air channel
13 plate
14 plate 15 exhaust air channel
16 cylinder section
17 fresh air channel
18 conditioning means
19 ultrafine distributing means
20 decontaminant
21 stock
22 pump
23 carrier air line
24 conditioner
25 plenum supply lines
26 plenum supply distributing line
27 manipulator supply lines
28 manipulator supply distributing line
29 shared supply line
30 junction
31 plenum valve
32 manipulator valve
33 nozzle
34 entry opening
35 exit openings
36 cone section
V vertical direction (vertical)

The invention claimed is:

1. A decontamination assembly (1) for pharmaceutical applications, comprising an isolator (2) having a manipulator chamber (3) and a plenum chamber (4) which is disposed above the manipulator chamber (3) and which can be supplied with an air flow (9) via at least one circulation fan (7) disposed in a circulating-air generation chamber, a membrane (5) for generating a laminar air flow (11) in the manipulator chamber (3) during a working operating state being disposed between the plenum chamber (4) and the manipulator chamber (3), the manipulator chamber (3) being connected to the circulating-air generation chamber (6) in an air-conducting manner via a return-air channel (12), further comprising ultrafine distributing means (19), for producing a decontaminant/air mixture based on a liquid decontaminant stock, the ultrafine distributing means (19) being connected to the plenum chamber (4) via at least one plenum supply line (25) leading into the plenum chamber (4) so as to directly supply the plenum chamber (4) with the decontaminant/air mixture when in a decontamination operating state, wherein
the ultrafine distributing means (19) are also connected directly to the manipulator chamber (3) via at least one manipulator supply line (27) so as to directly supply the manipulator chamber (3) with the decontaminant/air mixture when in the decontamination operating state, whereby the decontaminant air/mixture can be supplied to the plenum chamber (4) and the manipulator chamber (3) without operation of the at least one circulation fan (7), and wherein the at least one plenum supply line (25) and/or the at least one manipulator supply line (27) lead into the plenum chamber (4) and into the manipulator chamber (3), respectively, via a nozzle (33), each nozzle (33) having multiple outlet openings (35), which point in different directions and are distributed across a cone section (36) and cylinder section adjacent to the cone section (36).

2. The decontamination assembly according to claim 1, wherein multiple plenum supply lines (25) leading into the plenum chamber (4) at different locations and/or multiple manipulator supply lines (27) leading into the manipulator chamber (3) at different locations are provided.

3. The decontamination assembly according to claim 1, wherein the plenum chamber (4) and the manipulator chamber (3) can be simultaneously supplied with the decontaminant/air mixture via the at least one plenum supply line (25) and the at least one manipulator supply line (27).

4. The decontamination assembly according to claim 1, wherein valve means are assigned to the at least one plenum supply line (25) and/or to the at least one manipulator supply line (27), wherein the valve means can prevent air from flowing out of the plenum chamber (4) via the at least one plenum supply line (25) and the manipulator supply line (27) during the working operating state.

5. The decontamination assembly according to claim 1, wherein a plenum valve (31) disposed in an area between the ultrafine distributing means (19) and a plenum supply line outlet is assigned to the at least one plenum supply line (25) and/or wherein a manipulator valve (32) disposed in an area between the ultrafine distributing means (19) and a plenum supply line outlet is assigned to the at least one manipulator supply line (27).

6. The decontamination assembly according to claim 5, wherein the plenum valve (31) and/or the manipulator valve (32) are operable in a first state wherein the plenum chamber (4) and the manipulator chamber (3) can be supplied with the decontaminant/air mixture simultaneously and/or in a second state wherein the plenum chamber (4) and the manipulator chamber (3) can be supplied with the contaminant/air mixture one after the other, in a repeated alternating manner, and/or wherein a volumetric flow rate of the decontaminant/air-mixture volumetric flow flowing into the plenum chamber (4) and into the manipulator chamber (3) can be adjusted during the decontamination operating state.

7. The decontamination assembly according to claim 1, wherein the ultrafine distributing means (19) comprise a shared evaporator or a shared nebulizer which is connected to the plenum supply line (25) and to the manipulator supply line (27) or wherein the ultrafine distributing means (19) have separate evaporators or nebulizers for supplying the plenum supply line (25) and the manipulator supply line (27).

8. The decontamination assembly according to claim 1, wherein a filter (8) for suspended particles, via which the air flow (9) generated by the circulation fan (7) can be applied to the plenum chamber (4) is disposed between the plenum chamber (4) and the circulating-air generation chamber (6), which is disposed above the plenum chamber (4).

9. The decontamination assembly according to claim 1, wherein a catalytic converter (10) for degrading decontaminant (20) during circulating-air operation is assigned to the circulation fan (7).

10. The decontamination assembly according to claim 9, wherein the catalytic converter (10) is disposed stationary relative to the circulation fan (7) and a control for the circulation fan (7) is configured to control the circulation fan (7) in such a manner that the circulation fan (7) is switched off during the decontamination operating state, or wherein a bypass can be established between the catalytic converter (10) and the circulation fan (7), and wherein the control is configured to control the circulation fan (7) in such a manner that it is operated during the decontamination operating state when the bypass is established.

11. The decontamination assembly according to claim 1, wherein the ultrafine distributing means (19), which are disposed outside of the manipulator chamber (3) and/or of the plenum chamber (4) and/or of the circulating-air generation chamber (6), are connected to a carrier air line (23) for supplying the ultrafine distributing means (19) with carrier air, with sterile and/or conditioned carrier air, from outside the working chamber during the decontamination phase, the carrier air serving to absorb decontaminant vapor or to nebulize decontaminant.

12. The decontamination assembly according to claim 1, wherein the at least one manipulator supply line (27) leads into the manipulator chamber (3) in the area of a manipulator chamber side wall and/or wherein no pharmaceutical working unit or functional unit is disposed directly vertically below the manipulator supply line end.

13. The decontamination assembly according to claim 1, wherein the membrane (5) comprises a mesh.

14. The decontamination assembly according to claim 1, wherein the return-air channel (12) is disposed between two transparent plates (13, 14).

15. The decontamination assembly according to claim 1, wherein the ultrafine distributing means (19) is an evaporator or nebulizer.

16. The decontamination assembly according to claim 1, wherein the liquid decontamination stock is $H_2O_2$.

17. The decontamination assembly according to claim 9, wherein the at least one plenum supply line (25) leads into the plenum chamber (4) downstream of the catalytic converter (10).

18. The decontamination assembly according to claim 1, wherein the manipulator supply line (27) is unbranched from the ultrafine distributing means (19) to the manipulator chamber (3), the plenum supply line (25) is unbranched from the ultrafine distributing means (19) to the plenum chamber (4), and the manipulator supply line (27) and the plenum supply line (25) extend from the ultrafine distributing means (19) to the manipulator chamber (3) and the plenum chamber (4) respectively, and do not lead into or connect with any other feed or discharge line other than each other.

19. The decontamination assembly according to claim 8, wherein flow out of the manipulator chamber (3) passes through the return-air channel (12) to an exhaust air line (15) whereby, flow can exit the manipulator chamber (3) without passing the filter (8).

* * * * *